(12) United States Patent
Ghosh

(10) Patent No.: US 10,000,505 B2
(45) Date of Patent: Jun. 19, 2018

(54) ANTI-CANCER AGENTS AND PREPARATION THEREOF

(71) Applicant: Purdue Research Foundation, West Lafayette, IN (US)

(72) Inventor: Arun K. Ghosh, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days. days.

(21) Appl. No.: 15/038,027

(22) PCT Filed: Nov. 19, 2014

(86) PCT No.: PCT/US2014/066458
§ 371 (c)(1),
(2) Date: May 19, 2016

(87) PCT Pub. No.: WO2015/077370
PCT Pub. Date: May 28, 2015

(65) Prior Publication Data
US 2016/0297831 A1     Oct. 13, 2016

Related U.S. Application Data

(60) Provisional application No. 61/906,133, filed on Nov. 19, 2013.

(51) Int. Cl.
| | | |
|---|---|---|
| *A61K 31/336* | (2006.01) | |
| *A61K 31/35* | (2006.01) | |
| *A61K 31/495* | (2006.01) | |
| *A61K 31/535* | (2006.01) | |
| *C07D 493/10* | (2006.01) | |
| *C07D 407/12* | (2006.01) | |
| *A61K 31/5377* | (2006.01) | |
| *A61K 45/06* | (2006.01) | |
| *C07D 309/14* | (2006.01) | |
| *A61K 47/68* | (2017.01) | |

(52) U.S. Cl.
CPC .......... *C07D 493/10* (2013.01); *A61K 31/336* (2013.01); *A61K 31/35* (2013.01); *A61K 31/495* (2013.01); *A61K 31/535* (2013.01); *A61K 31/5377* (2013.01); *A61K 45/06* (2013.01); *A61K 47/6803* (2017.08); *C07D 309/14* (2013.01); *C07D 407/12* (2013.01)

(58) Field of Classification Search
CPC .... C07D 493/10; A61K 31/336; A61K 31/35; A61K 31/495; A61K 31/535
See application file for complete search history.

(56) References Cited

U.S. PATENT DOCUMENTS

| 7,825,267 B2 * | 11/2010 | Koide .................. C07D 303/12 549/332 |
| 8,309,599 B2 | 11/2012 | Koide et al. |
| 2011/0207604 A1 | 8/2011 | Asolkar et al. |

FOREIGN PATENT DOCUMENTS

| CN | 105829299 A | 8/2016 |
| IN | 201617020519 A | 8/2016 |
| JP | 2017503753 A | 2/2017 |
| WO | WO-2013032693 A2 | 3/2013 |
| WO | WO-2014068443 A1 | 5/2014 |
| WO | WO-2015077370 A1 | 5/2015 |

OTHER PUBLICATIONS

"International Application Serial No. PCT/US2014/066458, International Search Report dated Feb. 4, 2015", 3 pgs.
"International Application Serial No. PCT/US2014/066458, Written Opinion dated Feb. 4, 2015", 5 pgs.
Ghosh, et al., "?Enantfoselective Syntheses of FR901464 arid SpliceostatIn A: Potent Inhibitors of Spliceosome?", Ord. Lett. 15 (19), (Sep. 19, 2013), 5088?5091.
Horigome, "A synthesis of FR901464", Tetrahedron Letters 42, (2001), 8207-8210.
Koide, et al., "Total Syntheses of FR901464", Review Article, [Online] retrieved from the Internet: <https://www.jstage.jst.go.jp/article/yuklgoselkyokalshi1943/65/2/65_2_119/___pdf, (2007), p. 33-40.
Motoyoshi, "Total synthesis of FR901464: second generation", Tetrahedron 62, (200), 1378-1389.
"Colombian Application Serial No. 16-160.200, Office Action dated Nov. 8, 2016", 2 pgs.
"Colombian Application Serial No. 16-160.200, Response Filed Mar. 8, 2017 to Office Action dated Nov. 8, 2016", (W/ Translated Claims), 11 pgs.
"European Application Serial No. 14863201.1, Supplementary Partial European Search Report dated Apr. 6, 2017", 8 pgs.
"International Application Serial No. PCT/US2014/066458, International Preliminary Report on Patentability dated Jun. 2, 2016", 7 pgs.
"Vietnam Application Serial No. 1-2016-02239, Response filed Jan. 6, 2017 to Office Action dated Oct. 6, 2016".
Ghosh, Arun K, et al., "Enantioselective Syntheses of FR901464 and Spliceostatin A: Potent Inhibitors of Spliceosome", Organic Letters, 14(23), (Oct. 4, 2013), 5088-5091 pgs.
Osman, Sami, et al., "Structural Requirements for the Antiproliferative Activity of Pre-mRNA Splicing Inhibitor FR901464", Chemistry—A European Journal, vol. 17, No. 3, (Nov. 19, 2010), 895-904 pgs.
"Eurasian Application Serial No. 201691010, Office Action dated Jun. 7, 2017", W/ English Translation, 6 pgs (partial translation).
"European Application Serial No. 14863201.1, Extended European Search Report dated Aug. 4, 2017", 11 pgs.

\* cited by examiner

*Primary Examiner* — Yong S. Chong
(74) *Attorney, Agent, or Firm* — Schwegman Lundberg & Woessner, P.A.

(57) ABSTRACT

Embodiments of the present invention provide, among other compounds, a family of spliceosome-inhibiting compounds that can be used as therapeutic anti-cancer agents. The compounds are synthesized in a process that includes the catalytic cross metathesis of a cyclic epoxy alcohol to an amide.

9 Claims, No Drawings

ANTI-CANCER AGENTS AND PREPARATION THEREOF

CROSS-REFERENCE TO RELATED APPLICATIONS

This application is a U.S. National Stage Filing under 35 U.S.C. 371 from International Application No. PCT/US2014/066458, filed on Nov. 19, 2014, and published as WO 2015/077370 on May 28, 2015, which claims the benefit of priority to U.S. Provisional Appl. Ser. No. 61/906,133, filed Nov. 19, 2013, which applications are incorporated by reference as if fully set forth herein.

STATEMENT OF U.S. GOVERNMENT SUPPORT

This invention was made with government support under GM053386 awarded by the National Institutes of Health. The government has certain rights in the invention.

FIELD OF THE INVENTION

Embodiments of the present invention relate to compounds that can be used to treat disease, e.g., cancer, and compositions and prodrugs including, or resulting in, these compounds. Methods of making the compounds are also disclosed.

BACKGROUND

The American Cancer Society estimates that cancer costs the U.S. economy almost $200 billion per year due to the costs of medical treatment (about $80 billion per year) and lost productivity due to death and/or disability (about $120 billion per year). Of course, there is also a human toll as loved ones are diagnosed, treated, and sometimes die from many forms of cancer. Because of the high social and economic costs of cancer, new cancer treatments are a top priority for institutions such as the U.S. National Institutes of Health as well as major pharmaceutical companies.

SUMMARY

Proliferative diseases, such as cancer, cause harm to the body with the rapid growth of cells that interfere with the health function of nearby (or far-away) tissues. Because the cells replicate quickly, compounds that disrupt transcription pathways are valuable in fighting the disease. That is, if it is possible to disrupt the function of one or more proteins that play a role in a transcription pathway, the proliferation (and potential metastasis) of cancerous cells will be limited. Such a disruption would at least help a patient gain additional months or years of life.

One family of protein complexes involved in transcription pathways are spliceosomes. Spliceosomes typically include over 100 proteins that work together to control the excision of exons (i.e., splicing of introns) from genomic material during the transcription. Compounds that interfere with the function of spliceosomes or a spliceosome-regulation protein are valuable for slowing or stopping the spread of proliferative disease.

Embodiments of the present invention include compounds that are effective at limiting the growth of proliferative cells and useful as therapeutic cancer agents. Embodiments of the present invention also include compositions comprising these compounds as well as pro-drugs that result in the compounds when administered to a patient. The compounds are useful for the treatment of cancer, in particular solid tumor cell cancers, such as breast, lung, cervical, prostate, ovarian, pancreatic, and renal cell cancer. The compounds, compositions, and prodrugs can be administered to a patient in need of treatment for proliferative disease, e.g., cancer.

Embodiments of the present invention additionally include methods of making the therapeutic compounds of the various embodiments of the invention. The methods include the cross metathesis of an epoxy alcohol fragment with an amide fragment in the presence of a catalyst. In an embodiment, the method includes forming the epoxy alcohol fragment from an (R)-isopropylidene glyceraldyhyde, forming the amide fragment using a Corey-Bakshi-Shibata (CBS) reduction, an Achmatowicz rearrangement, a stereoselective Michael addition, and coupling the first and second fragments with a cross-metathesis reaction. The method can be performed in about 20 steps under standard reaction conditions and proceeds with high enantiomeric efficiency (>98% ee) and a good yield.

DETAILED DESCRIPTION

Embodiments of the invention include a family of novel compounds that can be used as therapeutic anti-cancer agents. The agents can be synthesized in a straightforward synthesis that includes a catalytic cross metathesis of a cyclic epoxy alcohol to a amide, as described herein.

Various embodiments of the present invention are directed to compounds having Formula I and stereoisomers, pharmaceutically acceptable salts, prodrugs (e.g., ester) or antibody conjugates (see, e.g., U.S. Pat. No. 8,663,643, which is incorporated by reference as if fully set forth herein) thereof:

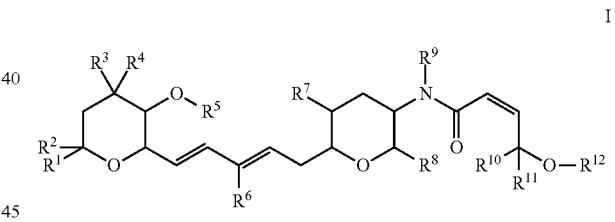

I wherein
$R^1$ and $R^2$ are independently selected from the group consisting of H, OH, $C_{1-6}$-alkyl, $C_{1-6}$-alkoxy, $C_{2-6}$-alkenyloxy, —$(CH_2)_nC(O)NR^{16}R^{17}$ (wherein $R^{16}$ and $R^{17}$ are selected independently from the group consisting of H, $C_{1-6}$-alkyl, and $C_{1-6}$-alkyl substituted with one to three groups independently selected from halo, hydroxy, $C_{1-6}$-alkoxy, and aryl; or $R^{16}$ and $R^{17}$, together with the nitrogen atom to which they are bound, form a 5- to 6-membered heterocyclic or heteroaromatic ring), and $C_{1-6}$-alkyl substituted with one to three groups independently selected from halo, hydroxy, $C_{1-6}$-alkoxy, and O-hydroxy protecting group;
$R^3$ and $R^4$ are selected independently from the group consisting of OH, $C_{1-6}$-alkyl (optionally substituted with Cl, F, $NO_2$, OH, or LG, wherein LG is a leaving group such as a —O-mesyl, —O-tosyl or —O-besyl leaving group), C(O)$R^{13}$, F, Cl, $NO_2$, wherein each $R^{13}$ is independently H or $C_{1-6}$-alkyl; or $R^3$ and $R^4$, together with the carbon atom to which they are bound, form an epoxide ring; $R^5$ and $R^{12}$ are independently selected from the group consisting of H, a hydroxyl protecting group, $C_{1-6}$-alkyl, C(O)$R^{13}$, C(O)O$R^{13}$, and C(O)NR$^{14}$R$^{15}$, wherein each R$^{13}$ is independently H or C$_{1-6}$-alkyl, and wherein R$^{14}$ and R$^{15}$ are selected independently from the group consisting of H and C$_{1-6}$-alkyl; or R$^{14}$ and R$^{15}$, together with the nitrogen atom to which they are bound, form a 5- to 6-membered heterocyclic or hetero aromatic ring;

R$^6$ is selected from the group consisting of H and C$_{1-6}$-alkyl; and

R$^7$ is C$_{1-6}$-alkyl; and

R$^8$, R$^9$, R$^{10}$, and R$^{11}$ are independently selected from the group consisting of H and C$_{1-6}$-alkyl.

Various other embodiments of the present invention are directed to compounds having Formula Ia and stereoisomers, pharmaceutically acceptable salts, prodrugs (e.g., ester) or antibody conjugates thereof:

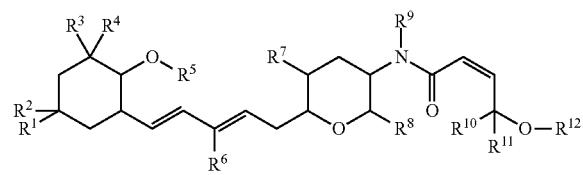

Ia wherein

R$^1$ and R$^2$ are independently selected from the group consisting of H, OH, C$_{1-6}$-alkyl, C$_{1-6}$-alkoxy, C$_{2-6}$-alkenyloxy, —(CH$_2$)$_n$C(O)NR$^{16}$R$^{17}$ (wherein R$^{16}$ and R$^{17}$ are selected independently from the group consisting of H, C$_{1-6}$-alkyl, and C$_{1-6}$-alkyl substituted with one to three groups independently selected from halo, hydroxy, C$_{1-6}$-alkoxy, and aryl; or R$^{16}$ and R$^{17}$, together with the nitrogen atom to which they are bound, form a 5- to 6-membered heterocyclic or heteroaromatic ring), and C$_{1-6}$-alkyl substituted with one to three groups independently selected from halo, hydroxy, C$_{1-6}$-alkoxy, and O-hydroxy protecting group;

R$^3$ and R$^4$ are selected independently from the group consisting of OH, C$_{1-6}$-alkyl (optionally substituted with Cl, F, NO$_2$, OH, or LG, wherein LG is a leaving group such as a —O-mesyl, —O-tosyl or —O-besyl leaving group), C(O)R$^{13}$, F, Cl, NO$_2$, wherein each R$^{13}$ is independently H or C$_{1-6}$-alkyl; or R$^3$ and R$^4$, together with the carbon atom to which they are bound, form an epoxide ring;

R$^5$ and R$^{12}$ are independently selected from the group consisting of H, a hydroxyl protecting group, C$_{1-6}$-alkyl, C(O)R$^{13}$, C(O)OR$^{13}$, and C(O)NR$^{14}$R$^{15}$, wherein each R$^{13}$ is independently H or C$_{1-6}$-alkyl, and wherein R$^{14}$ and R$^{15}$ are selected independently from the group consisting of H and C$_{1-6}$-alkyl; or R$^{14}$ and R$^{15}$, together with the nitrogen atom to which they are bound, form a 5- to 6-membered heterocyclic or hetero aromatic ring;

R$^6$ is selected from the group consisting of H and C$_{1-6}$-alkyl; and

R$^7$ is C$_{1-6}$-alkyl; and

R$^8$, R$^9$, R$^{10}$, and R$^{11}$ are independently selected from the group consisting of H and C$_{1-6}$-alkyl.

Still other embodiments of the present invention are directed to a process for preparing a compound having Formula I and a stereoisomer, pharmaceutically acceptable salt, prodrug (e.g., ester) or antibody conjugate thereof:

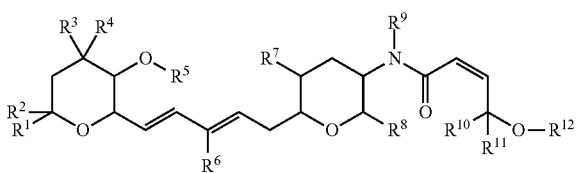

I wherein

R$^1$ and R$^2$ are independently selected from the group consisting of H, OH, C$_{1-6}$-alkyl, C$_{1-6}$-alkoxy, C$_{2-6}$-alkenyloxy, —(CH$_2$)$_n$C(O)NR$^{16}$R$^{17}$ (wherein R$^{16}$ and R$^{17}$ are selected independently from the group consisting of H, C$_{1-6}$-alkyl, and C$_{1-6}$-alkyl substituted with one to three groups independently selected from halo, hydroxy, C$_{1-6}$-alkoxy, and aryl; or R$^{14}$ and R$^{15}$, together with the nitrogen atom to which they are bound, form a 5- to 6-membered heterocyclic or heteroaromatic ring), and C$_{1-6}$-alkyl substituted with one to three groups independently selected from halo, hydroxy, C$_{1-6}$-alkoxy, and O-hydroxy protecting group;

R$^3$ and R$^4$ are selected independently from the group consisting of OH, C$_{1-6}$-alkyl (optionally substituted with Cl, F, NO$_2$, OH, or LG, wherein LG is a leaving group such as a —O-mesyl, —O-tosyl or —O-besyl leaving group), C(O)R$^{13}$, F, Cl, NO$_2$, wherein each R$^{13}$ is independently H or C$_{1-6}$-alkyl; or R$^3$ and R$^4$, together with the carbon atom to which they are bound, form an epoxide ring;

R$^5$ and R$^{12}$ are independently selected from the group consisting of H, a hydroxyl protecting group, C$_{1-6}$-alkyl, C(O)R$^{13}$, C(O)OR$^{13}$, and C(O)NR$^{14}$R$^{15}$, wherein each R$^{13}$ is independently H or C$_{1-6}$-alkyl, and wherein R$^{14}$ and R$^{15}$ are selected independently from the group consisting of H and C$_{1-6}$-alkyl; or R$^{14}$ and R$^{15}$, together with the nitrogen atom to which they are bound, form a 5- to 6-membered heterocyclic or hetero aromatic ring;

R$^6$ is selected from the group consisting of H and C$_{1-6}$-alkyl; and

R$^7$ is C$_{1-6}$-alkyl;

R$^8$, R$^9$, R$^{10}$ and R$^{11}$ are independently selected from the group consisting of H and C$_{1-6}$-alkyl;

the method comprising converting a compound of the Formula II:

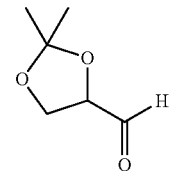

II to a compound of the Formula III:

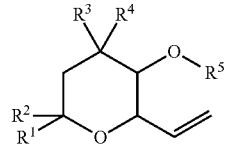

III wherein $R^1$, $R^2$, $R^3$, $R^4$, and $R^5$ are each defined herein; and contacting a compound of Formula III with a compound of the Formula IV:

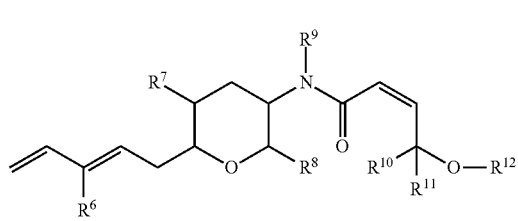

IV wherein $R^6$, $R^7$, $R^8$, $R^9$, $R^{10}$, $R^{11}$, and $R^{12}$ are defined herein; in the presence of an olefin metathesis catalyst to form a compound of Formula I.

As used herein, the term "$C_{1-6}$-alkyl" refers to monovalent saturated aliphatic hydrocarbyl groups having from 1 to 6 carbon atoms. This term includes, but is not limited to, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). The term $C_{1-6}$-alkyl also includes cycloalkyl groups including, but not limited to, cyclopropyl, cyclobutyl, cyclopentyl, and cyclohexyl.

As used herein, the term "$C_{2-6}$-alkenyl" (e.g., in $C_{2-6}$-alkenyloxy) in refers to monovalent unsaturated hydrocarbyl groups having from 2 to 6 carbon atoms. This term includes, but is not limited to, linear and branched hydrocarbyl groups such as vinyl ($CH_2$=CH—), propenyl ($CH_2$=$CH_2CH_2$—), and isopropenyl (($CH_3)(CH_2)C$—). The term $C_{2-6}$-alkyl also includes cycloalkenyl groups including, but not limited to, cyclopentenyl and cyclohexenyl.

The term "heteroaryl" as used herein refers to an aromatic heterocycle ring of 5 to 14 members, such as 5 to 6 members, having at least one heteroatom selected from nitrogen, oxygen and sulfur, and containing at least 1 carbon atom. Heteroaryls may be monocyclic, bicyclic, or tricyclic ring systems. Representative heteroaryls are triazolyl, tetrazolyl, oxadiazolyl, pyridyl, furyl, benzofuranyl, thiophenyl, benzothiophenyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, pyrimidyl, azepinyl, oxepinyl, and quinoxalinyl.

As used herein, the term "aryl" broadly refers to cyclic aromatic hydrocarbons that do not contain heteroatoms in the ring. Such aryl groups may be substituted or unsubstituted. Aryl groups include, but are not limited to, phenyl, biphenyl, fluorenyl, phenanthrenyl, and naphthyl groups.

As used herein, the term "heterocycle" or "heterocycloalkyl" as used herein refers to 5- to 14-membered ring systems, such as 5- to 6-membered ring systems, which are either saturated, unsaturated, and which contain from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles may be monocyclic, bicyclic, or tricyclic ring systems. The bicyclic or tricyclic ring systems may be spiro-fused. The bicyclic and tricyclic ring systems may encompass a heterocycle or heteroaryl fused to a benzene ring. The heterocycle may be attached via any heteroatom or carbon atom. Heterocycles include heteroaryls as defined above. Representative examples of heterocycles include, but are not limited to, aziridinyl, oxiranyl, thuiranyl, triazolyl, tetrazolyl, azirinyl, diaziridinyl, diazirinyl, oxaziridinyl, azetidinyl, azetidinonyl, oxetanyl, thietanyl, piperidinyl, piperazinyl, morpholinyl, pyrrolyl, oxazinyl, thiazinyl, diazinyl, dioxanyl, triazinyl, tetrazinyl, imidazolyl, tetrazolyl, pyrrolidinyl, isoxazolyl, furanyl, furazanyl, pyridinyl, oxazolyl, benzoxazolyl, benzisoxazolyl, thiazolyl, benzthiazolyl, thiophenyl, pyrazolyl, triazolyl, pyrimidinyl, benzimidazolyl, isoindolyl, indazolyl, benzodiazolyl, benzotriazolyl, benzoxazolyl, benzisoxazolyl, purinyl, indolyl, isoquinolinyl, quinolinyl, and quinazolinyl.

The term "hydroxy" refers to the group —OH.

The term "hydroxy protecting group" refers to protecting groups for an —OH group. Suitable hydroxy protecting groups as well as suitable conditions for protecting and deprotecting particular functional groups are well known in the art. For example, numerous such protecting groups are described in T. W. Greene and P. G. M. Wuts, PROTECTING GROUPS IN ORGANIC SYNTHESIS, 3rd ed., Wiley, New York. Such hydroxy protecting groups include $C_{1-6}$ alkyl ethers, benzyl ethers, p-methoxybenzyl ethers, silyl ethers, and the like.

The term "$C_{1-6}$-alkoxy" refers to the group —O—($C_{1-6}$-alkyl) wherein $C_{1-6}$-alkyl is defined herein. $C_{1-6}$-alkoxy includes, but is no limited to, methoxy, ethoxy, n-propoxy, isopropoxy, n-butoxy, t-butoxy, sec-butoxy, and n-pentoxy.

In some embodiments, a compound of the Formula III is a compound of the formula:

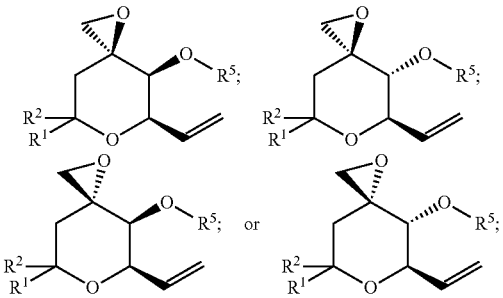

wherein $R^1$, $R^2$, and $R^5$ are defined herein.

In some embodiments, a compound of the Formula IV is a compound of the formula:

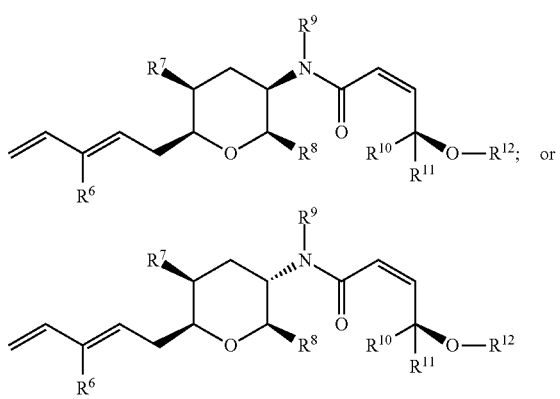

wherein $R^6$-$R^{12}$ are defined herein.

In some embodiments, the compound of Formula IV, or a stereoisomer, pharmaceutically acceptable salt, prodrug (e.g., ester) or antibody conjugate thereof, is prepared from a compound of the Formula V:

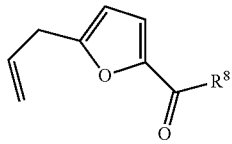

V wherein $R^8$ is defined herein. The compound of the Formula IV can be prepared via process comprising:

contacting a compound of the Formula V with a suitable reducing agent (e.g., a Corey-Bakshi-Shibata (CBS) reduction using borane and a chiral oxazaborolidine) to obtain a compound of the Formula VI:

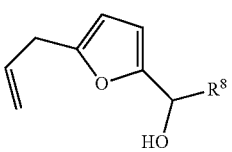

VI wherein $R^8$ is defined herein;

contacting the compound of the Formula VI with a suitable metal catalyst (e.g., VO(acac)$_2$ to effect an Achmatowicz rearrangement) to obtain a compound of the Formula VII:

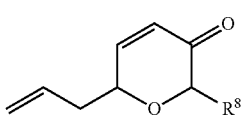

VII wherein $R^8$ is defined herein;

contacting the compound of the Formula VII with a compound of the R$^7$Li, wherein $R^7$ is defined herein, with a suitable metal salt (e.g., CuBr.S(CH$_3$)$_2$) to obtain a compound of the Formula VIII:

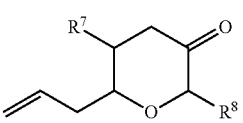

VIII contacting the compound of the Formula VIII with a suitable olefin metathesis catalyst (e.g., a suitable Grubbs' second generation olefin metathesis catalyst), wherein $R^7$ and $R^8$ are defined herein, to obtain a compound of the Formula IX:

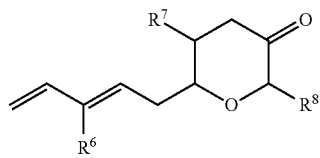

IX wherein $R^6$, $R^7$, and $R^8$ are defined herein;
converting the compound of the Formula IX to a compound of the Formula X:

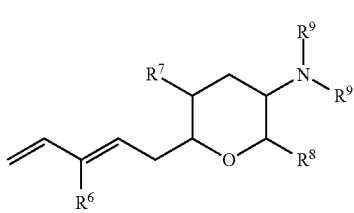

X wherein $R^6$, $R^7$, $R^8$, and $R^9$ are defined herein, under reductive amination conditions; and
contacting the compound of the Formula X with a compound of the Formula XI:

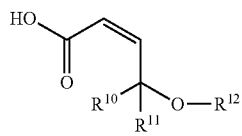

XI to obtain a compound of the Formula IV.

In some embodiments, the compound of the Formula VI is a compound of the formula:

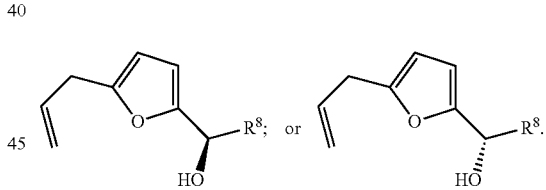

In some embodiments, the compound of the Formula VII is a compound of the formula:

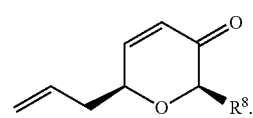

In some embodiments, the compound of the Formula VIII is a compound of the formula:

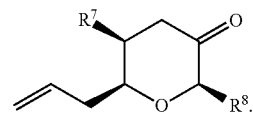

In some embodiments, the compound of the Formula IX is a compound of the formula:

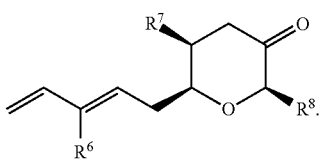

In some embodiments, the compound of the Formula X is a compound of the formula:

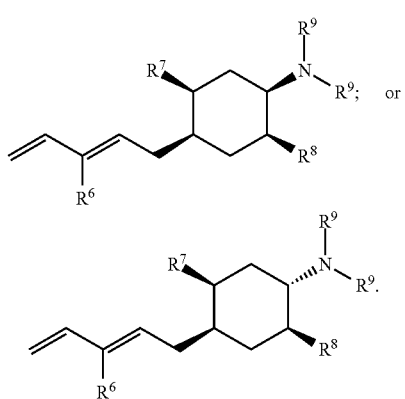

In some embodiments, the compound of the Formula XI is a compound of the formula:

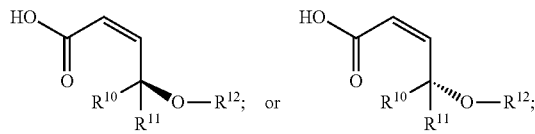

In some embodiments, the compound of the Formula I is a compound of the formula:

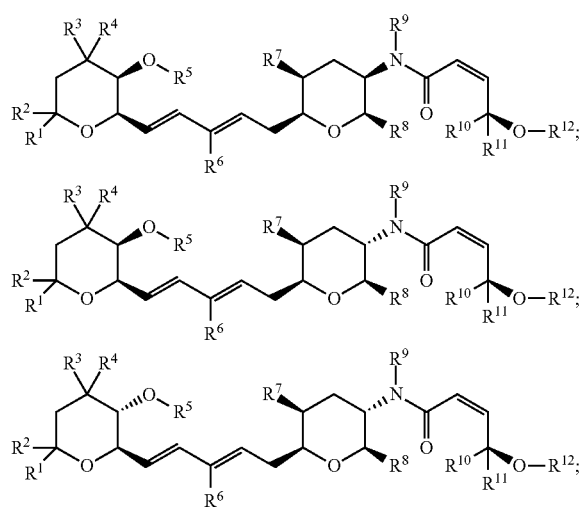

or a pharmaceutically acceptable salt, prodrug (e.g., ester) or antibody conjugate thereof.

In other embodiments, the compound of the Formula I is a compound of the formula:

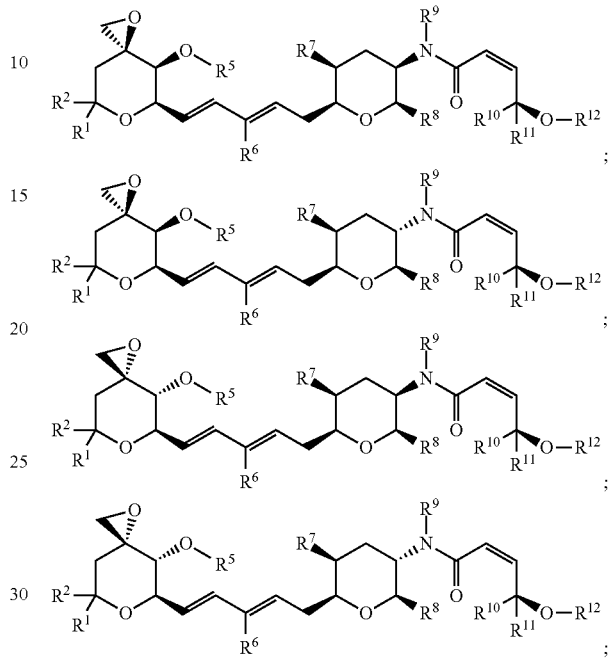

or a pharmaceutically acceptable salt, prodrug (e.g., ester) or antibody conjugate thereof.

Embodiments of the invention include any one of compounds Z1-Z7, as well as combinations thereof, which are potent spliceo some inhibitors, and may be administered as anti-cancer agents and which can be synthesized by the methods described herein:

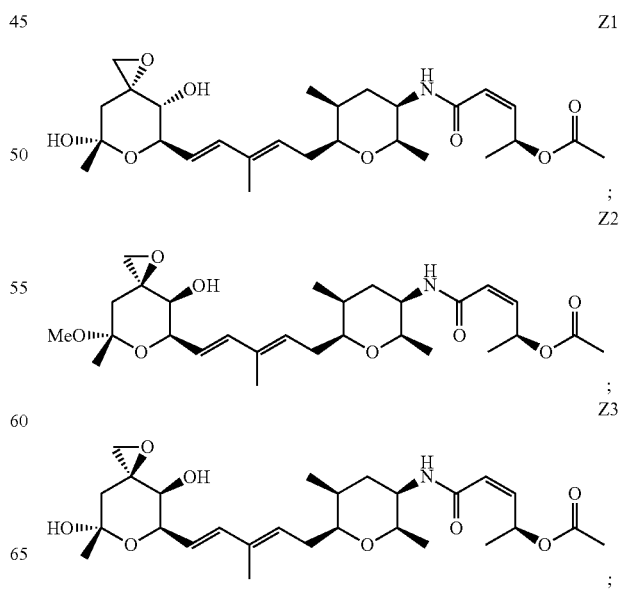

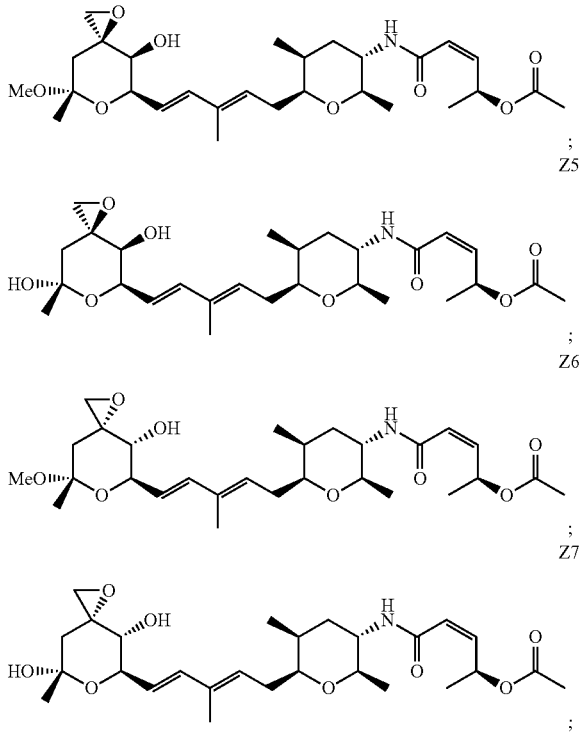

and pharmaceutically acceptable salts, prodrugs (e.g., ester) or antibody conjugates thereof. The compounds may be included in a composition or delivered as a prodrug. The compounds Z1-Z7 can be prepared via the processes described herein for compounds of the Formula I.

"Pharmaceutically acceptable salt" generally refers to pharmaceutically acceptable salts of a compound, which salts are derived from a variety of organic and inorganic counter ions well known in the art and include, by way of example only, sodium, potassium, calcium, magnesium, ammonium, and tetraalkylammonium; and when the molecule contains a basic functionality, salts of organic or inorganic acids, such as hydrochloride, hydrobromide, tartrate, mesylate, acetate, maleate, and oxalate.

As used herein, the term "prodrug" means a derivative of a compound that can hydrolyze, oxidize, or otherwise react under biological conditions (in vitro or in vivo) to provide an active compound, particularly a compound of the embodiments of the present invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Those of ordinary skill in the art will recognize that compounds described herein (e.g., compounds Z1-Z7) contain chiral centers. All diastereomers of the compounds described herein are contemplated herein, as well as racemates. Those of ordinary skill in the art will also recognize that compounds described herein (e.g., compounds Z1-Z7) comprise at three two double bonds each of which can have the E (engegen) or the Z (zusammen) configuration. All isomers of the compounds described herein (e.g., E,E,E; Z,Z,Z; E,Z,E; E,E,Z; Z,E,E; Z,E,Z, and Z,Z,E) are contemplated herein.

Various embodiments of the present invention also contemplate pharmaceutical compositions comprising one or more compounds of the various embodiments of the present invention (e.g. compounds Z1-Z7) and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multilayer tablets, bi-layer tablets, capsules, soft gelatin capsules, hard gelatin capsules, caplets, lozenges, chewable lozenges, beads, powders, gum, granules, particles, microparticle s, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

In some embodiments, the various embodiments of the present invention contemplate compositions comprising a therapeutically effective amount of one or more compounds of the various embodiments of the present invention (e.g. at least one compound Z1-Z7). In some embodiments, the compositions are useful in a method for treating cancer, the method comprising administering a therapeutically effective amount of one or more compounds of the various embodiments of the present invention to a patient in need thereof. In some aspects, the various embodiments of the present invention contemplate a compound of the various embodiments of the present invention for use as a medicament for treating a patient in need of relief from cancer. In some embodiments, the cancer includes, but is not limited to, solid tumor cell cancers including, but not limited to, pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkins disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes, such as breast, lung, cervical, prostate, ovarian, pancreatic, and renal cell cancer.

The term "therapeutically effective amount" as used herein, refers to that amount of one or more compounds of the various embodiments of the present invention (e.g. at least one compound Z1-Z7) that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

In some embodiments, a therapeutically effective amounts of the compounds of the various embodiments of the present invention can range from approximately 0.05 to 50 mg per kilogram body weight of the recipient per day; such as about 0.1-25 mg/kg/day, or from about 0.5 to 10 mg/kg/day. Thus, for administration to a 70 kg person, for instance, the dosage range can be about 35-70 mg per day.

In some embodiments, one or more of the compounds of the various embodiments of the present invention can be administered in combination with at least one other anticancer agent including, but not limited to docetaxel, paclitaxel, bevacizumab (Avastin™).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes. Such documents include, but are not limited to:
(1) (a) Nakajima, H.; Sato, B.; Fujita, T.; Takase, S.; Terano, H.; Okuhara, M. J. Antibiot. 1996, 49, 1196-1203. (b) Nakajima, H.; Hori, Y.; Terano, H.; Okuhara, M.; Manda, T.; Matsumoto, S.; Shimomura, K. J. Antibiot. 1996, 49, 1204-1211. (c) Nakajima, H.; Takase, S.;
Terano, H.; Tanaka, H. J. Antibiot. 1997, 50, 96-99.
(2) (a) Motoyoshi, H.; Horigome, M.; Ishigami, K.; Yoshida, T.; Horinouchi, S.; Yoshida, M.; Watanabe, H.; Kitahara, T. Biosci. Biotechnol. Biochem. 2004, 68, 2178-2182. (b) Kaida, D.; Motoyoshi, H.; Tashiro, E.; Nojima, T.; Hagiwara, M.; Ishigami, K.; Watanabe, H.; Kitahara, T.; Yoshida, T.; Nakajima, H.; Tani, T.; Horinouchi, S.; Yoshida, M. Nature Chem. Biol. 2007, 3, 576-583. (c) Zhang, F.; He, H.-Y.; Tang, M.-C.; Tang, Y.-M.; Zhou, Q.; Tang, G.-L. J. Am. Chem. Soc. 2011, 133, 2452-2462. (d) Fan, L.; Lagisetti, C.; Edwards, C. C.; Webb, T. R.; Potter, P. M. ACS Chem. Biol. 2011, 6, 582-589.
(3) (a) Thompson, C. F; Jamison, T. F.; Jacobsen, E. N. J. Am. Chem. Soc. 2000, 122, 10482-10483. (b) Thompson, C. F.; Jamison, T. F.; Jacobsen, E. N. J. Am. Chem. Soc. 2001, 123, 9974-9983.

(4) (a) Horigome, M.; Motoyoshi, H.; Watanabe, H.; Kitahara, T. Tetrahedron Lett. 2001, 42, 8207-8210. (b) Motoyoshi, H.; Horigome, M.; Watanabe, H.; Kitahara, T. Tetrahedron 2006, 62, 1378-1389.
(5) (a) Albert, B. J.; Koide, K. Org. Lett. 2004, 6, 3655-3658. (b) Albert, B. J.; Sivaramakrishnan, A.; Naka, T.; Koide, K. J. Am. Chem. Soc. 2006, 128, 2792-2793. (c) Albert, B. J.; Sivaramakrishnan, A.; Naka, T.; Czaicki, N. L.; Koide, K. J. Am. Chem. Soc. 2007, 129, 2648-2659.
(6) (a) Ghosh, A. K.; Anderson, D. D. Org. Lett. 2012, 14, 4730-4733. (b) Ghosh, A. K.; Li, J. Org. Lett. 2011, 13, 66-69.
(7) (a) Chatterjee, A. K.; Choi, T.-L.; Sanders, D. P.; Grubbs, R. H. J. Am. Chem. Soc. 2003, 125, 11360-11370. (b) Prunet, J. Curr. Top. Med. Chem. 2005, 5, 1559-1577.
(8) Organic Synthesis; Wiley: New York, 1998; Collect. Vol. IX, p 6; Org. Synth. 1995, 72, 6.
(9) (a) Achmatowicz, O.; Bukowski, P.; Szechner, B.; Zwierzchowska, Z.; Zamojski, A. Tetrahedron 1971, 27, 1973-1996. (b) Georgiadis, M. P.; Albizati, K. F.; Georgiadis, T. M. Org. Prep. Proc. Int. 1992, 24, 95-118.
(10) Trost, B. M.; Quintard, A. Org. Lett. 2012, 14, 4698-4700.
(12) Chen, Z.-H.; Tu, Y.-Q.; Zhang, S.-Y.; Zhang, F.-M. Org. Lett. 2011, 13, 724-727.
(13) Zhang, Y.; Rohanna, J.; Zhou, J.; Lyer, K.; Rainier, J. D. J. Am. Chem. Soc. 2011, 133, 3208-3216.
(14) Williams, D. R.; Fultz, M. W. J. Am. Chem. Soc. 2005, 127, 14550-14551.
(15) Prasad, K. R.; Gholap, S. L. J. Org. Chem. 2008, 73, 2-11.
(17) (a) Corey, E. J.; Chaykovsky, M. J. Am. Chem. Soc. 1965, 87, 1353-1364. (b) Alcaraz, L.; Harnett, J. J.; Mioskowski, C.; Martel, J. P.; Le gall, T.; Shin, D.-S.; Falck, J. R. Tetrahedron Lett. 1994, 35, 5449-5452.
(18) Bode, J. W.; Carreira, E. M. J. Org. Chem. 2001, 66, 6410-6424.
(19) (a) Williams, D. R.; Jass, P. A.; Tse, H.-L. A.; Gaston, R. D. J. Am. Chem. Soc. 1990, 112, 4552-4554. (b) Smith, A. B., III; Lin, Q.; Doughty, V. A.; Zhuang, L.; McBriar, M. D.; Kerns, J. K.; Brook, C. S.; Murase, N.; Nakayama, K. Angew. Chem., Int. Ed. 2001, 40, 196-199.
(20) Horita, K.; Yoshioka, T.; Tanaka, T.; Oikawa, Y.; Yonemitsu, O. Tetrahedron 1986, 42, 3021-3028.
(21) (a) Corey, E. J.; Roberts, B. E. J. Am. Chem. Soc. 1997, 119, 12425-12431. (b) Gazaille, J. A.; Abramite, J. A.; Sammakia, T. Org. Lett. 2012, 14, 178-181.
(22) Lewis, M. D.; Cha, J. K.; Kishi, Y. J. Am. Chem. Soc. 1982, 104, 4976-4978.
(23) Woodward, S. Chem. Soc. Rev. 2000, 29, 393-401.
(24) Ghosh, A. K.; Nicponski, D. R. Org. Lett. 2011, 13, 4328-4331.
(25) Scholl, M.; Ding, S.; Lee, C. W.; Grubbs, R. H. Org. Lett. 1999, 1, 953-956.
(26) Paquette, L. A.; Gugelchuk, M.; McLaughlin, M. L. J. Org. Chem. 1987, 52, 4732-4740. (27) Rafferty, R. J.; Williams, R M J Org. Chem. 2012, 77, 519-524. And
(28) DeChristopher, B. A.; Loy, B. A.; Marsden, M. D.; Schrier, A. J.; Zack, J. A.; Wender, P. A. Nature Chem. 2012, 4, 705-710. All of which are incorporated by reference in their entireties.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

The present invention can be better understood by reference to the following example which is offered by way of illustration. The present invention is not limited to the example(s) given herein.

A synthetic scheme for compounds Z1-Z7 is shown below with respect to FR901464 (1) and Spliceostatin A (2), shown below, which are not compounds of the invention.

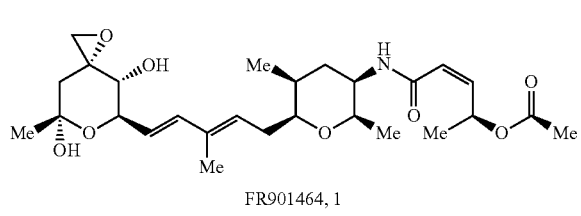

FR901464, 1

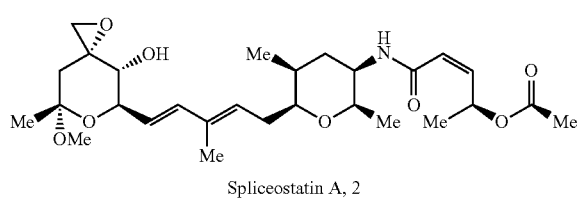

Spliceostatin A, 2

Nonetheless, it should be understood that the synthetic scheme is generally unique, and greatly simplifies the synthetic steps as compared to, e.g., the total synthesis of 1 described by Thompson, C. F., et al., *J. Am. Chem. Soc.* 122 10482-10483 (2000); and Thompson, C. F., et al., *J. Am. Chem. Soc.* 123: 9974-9983 (2001), both of which are incorporated by reference as if fully set forth herein. Compounds Z1-Z7 can be synthesized by making suitable substitutions in the synthesis of the cyclic epoxy alcohol (compound 3 in Scheme 1) as shown in Scheme 1 herein.

Example 1: Synthesis of Epoxy Alcohol Segment 3

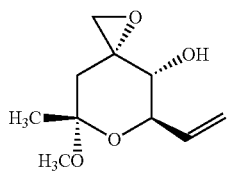

The synthesis of epoxy alcohol segment 3 is shown in Scheme 1. Commercially available bromo ketone 11 was protected as its dithiane derivative. Lithiation of the resulting dithiane with t-BuLi at 78° C. for 1 hours followed by reaction with (R)-isopropylidene glyceraldehyde provided a mixture (1:1) of diastereomers 12 and 13 in 61% yield in two steps. This lack of stereoselectivity was somewhat unexpected, especially given the presence of chelating atoms at both R and β positions of (R)-isopropylidene glyceraldehyde. In an attempt to improve antidiastereoselectivity, we investigated this addition reaction in the presence of a number of Lewis acids such as $CeCl_3$, $ZnCl_2$, and $MgBr_2$, in THF and ether. However, there was no further improvement in the diastereomeric ratio.

The isomers were separated by silica gel chromatography. The syn-isomer 12 was converted to desired anti-isomer 13 by a Mitsunobu reaction in the presence of p-nitrobenzoic acid followed by NaOH-mediated hydrolysis of the benzoate ester. The hydroxyl group of 13 was protected as a paramethoxy benzyl (PMB) ether, and subsequent removal of the isopropylidene group was carried out by the addition of p-TsOH in a one pot operation to provide diol 14. The primary alcohol was selectively mono-tosylated using tosyl chloride (TsCl) and $Et_3N$ in the presence of dibutyltin oxide. Reaction of the resulting mono-tosylate with an excess of Corey-Chaykovsky dimethylsulfonium, methylide prepared by treatment of trimethylsulfonium iodide with n-BuLi, furnished allylic alcohol 15 in 84% yield. A similar functional group transformation was previously reported by Carreira and co-workers. See Bode, J. W. and Carreira E. M., *J. Org. Chem.* 66: 6410-6424 (2001), which is incorporated by reference as if fully set forth herein. The dithiane group of 15 was then removed by using an excess of $Hg(ClO_4)_2$ in methanol in the presence of dry 2,6-lutidine. This condition resulted in the formation of the corresponding methyl ketal as a mixture of anomers, which upon treatment with a catalytic amount of p-TsOH in methanol at 0° C. provided a single diastereomer 16. Removal of the PMB group in 16 with 2,3-Dichloro-5,6-dicyano-1,4-benzoquinone (DDQ) followed by alcohol directed epoxidation with m-chloroperbenzoic acid (m-CPBA) afforded the desired epoxy alcohol segment 3 stereoselectively as a white solid in 19% overall yield from 11 (8 steps). The methyl ketal 3 is quite stable and easy to handle for subsequent reactions.

SCHEME 1

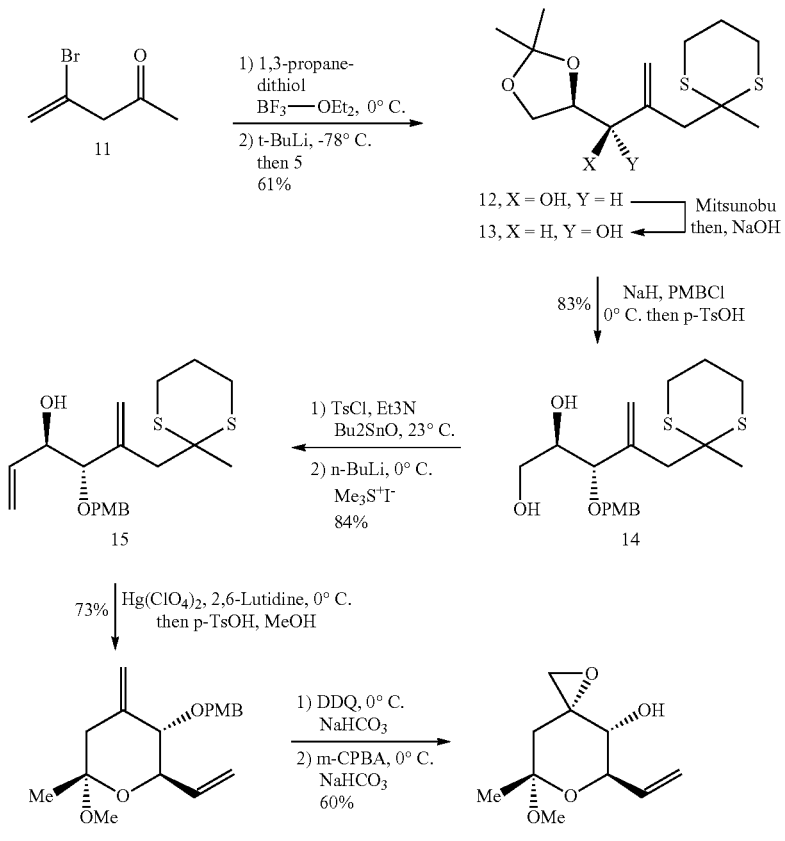

Example 2: Synthesis of Amide 4

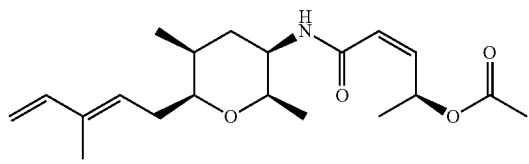

Amide 4 can be synthesized in a two-step process, shown below as Scheme 2A and Scheme 2B. The preparation of the Z-allylic acetate side chain 7 is shown in Scheme 2A. Optically active alcohol 10 was efficiently prepared by utilizing a catalytic asymmetric addition protocol reported by Trost and co-workers to provide 10>98% enantiomeric efficiency (ee). Saponification of methyl ester 10 with aqueous LiOH followed by acetylation with acetyl chloride provided acetate 17 in excellent yield. Hydrogenation over Lindlar's catalyst afforded the desired cis-alkene 7.

SCHEME 2A

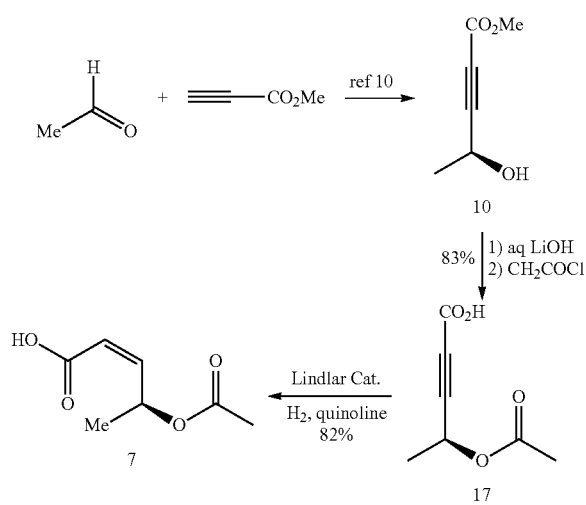

The synthesis of amide segment 4 is shown in Scheme 2B, where the amide segment 4 has the structure:

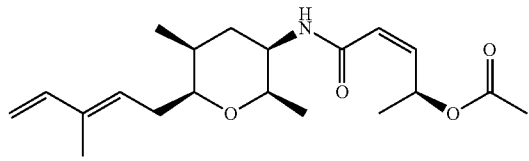

Enantioselective reduction of commercially available acetyl furan 18 with (S)-2-Me-CBS catalyst (also known as (S)-5,5-Diphenyl-2-methyl-3,4-propano-1,3,2-oxazaborolidine) and $BH_3 \cdot Me_2S$ afforded chiral alcohol 9 in 94% yield (93% ee). An Achmatowicz rearrangement was then carried out by treatment of alcohol 9 with $t\text{-}BuO_2H$ in the presence of a catalytic amount of $VO(acac)_2$ to furnish a hemiketal, which was directly reduced to enone 19 as a single diastereomer by employing the protocol described by Kishi and co-workers. Our subsequent synthetic plan required installation of the C20 (S)-methyl-bearing stereocenter. We elected to carry out a 1,4-addition to enone 19. Accordingly, treatment of 19 with $MeLi/CuBr \cdot Me_2S$ at $-78°$ C. for 2 hours provided the desired pyranone 8 in excellent yield (92%) and diastereoselectivity (25:1 dr, by $^1H$ and $^{13}C$ NMR analysis). The observed diastereoselectivity can be explained based upon the conformational analysis of enone 19. The stereochemical outcome of Michael addition can be rationalized by assuming stereoelectronically favorable axial attack of the cuprate as shown in the transition-state model 20.

Pyranone 8 and known alkene 21 were then subjected to cross-metathesis conditions using a Grubbs'-type second generation catalyst (Scholl, M., et al., *Org. Lett.* 1: 953-956 (1999), incorporated by reference as if fully set forth herein):

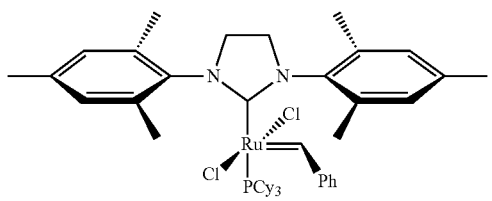

to provide the corresponding terminal tosylate. Treatment of the resulting tosylate with t-BuOK in DMSO at 75° C. for 12 hours resulted in diene 22 via base promoted elimination in 41% yield over two steps. Reductive amination of 22 with ammonium acetate and $NaBH_3CN$ afforded the corresponding primary amine 6 as a major product (6:1 dr, by $^1H$ and $^{13}C$ NMR analysis). The crude amine 6 and its epimer were directly treated with acid 7 using standard amidation conditions to give the amide 4 along with minor C-14 epimer, which were separated by column chromatography.

SCHEME 2B

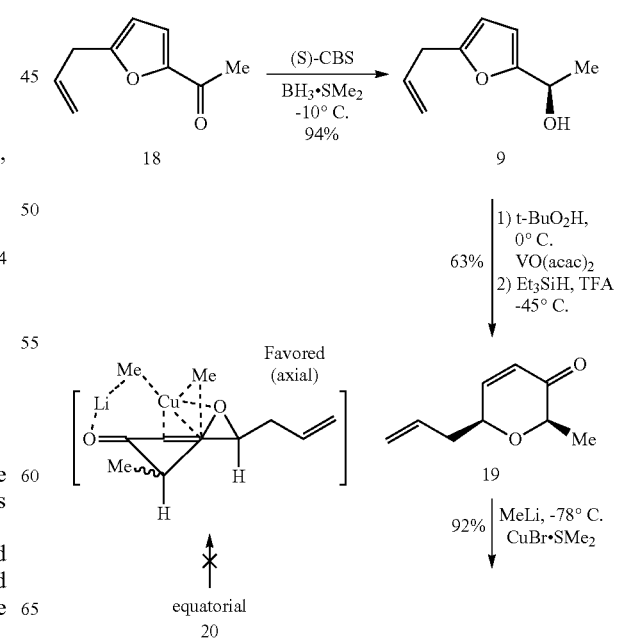

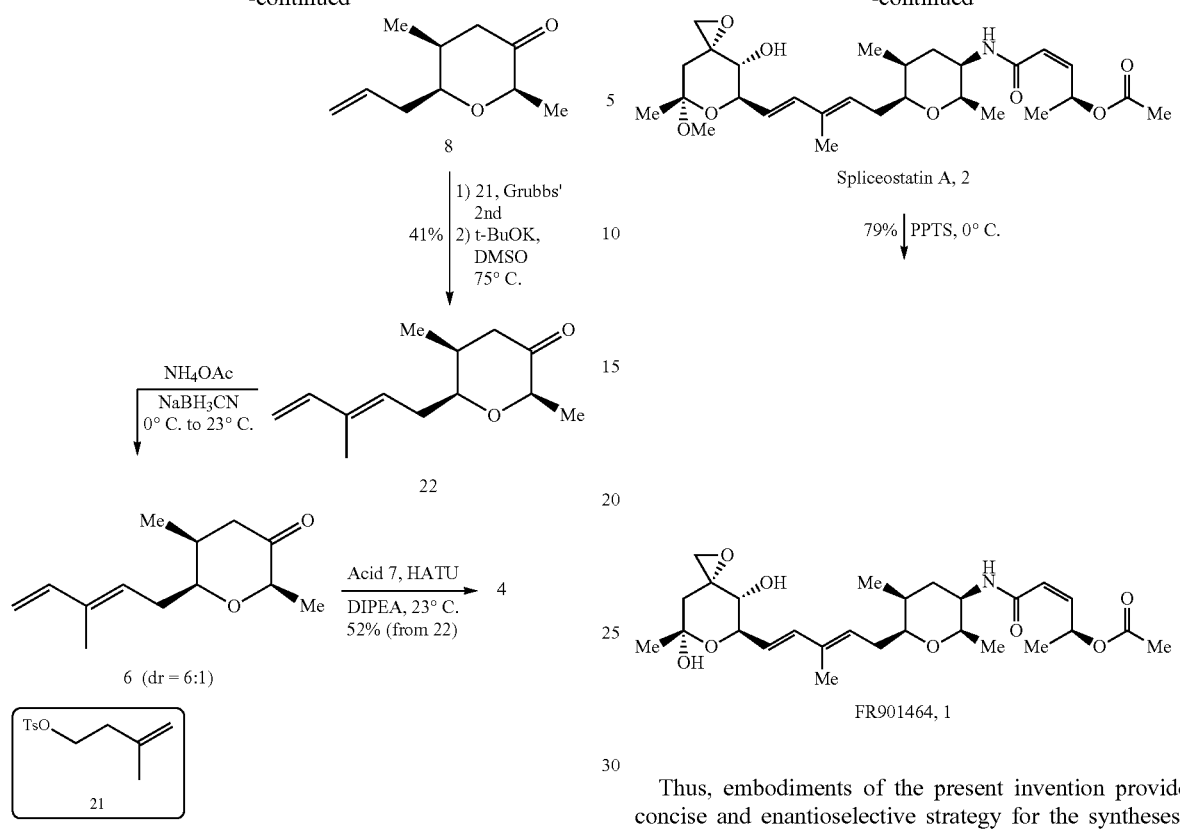

In the final step, FR901464 (1), Spliceostatin A (2), a compound of the invention, i.e., compounds Z1-Z7, or similar compounds can be created with the cross-metathesis of the epoxy alcohol segment 3 and the amide segment 4, as shown in Scheme 3. With the stereoselective syntheses of segments epoxy alcohol 3 (Scheme 1) and amide 4 (Scheme 2A/B), we then turned our attention to construct the C6-C7 double bond of the target molecules. As shown in Scheme 3, cross-metathesis of the two fragments proceeded smoothly in the presence of Grubbs' second-generation catalyst to afford spliceostatin A (2) as a white solid in 57% isolated yield based upon one recycle of unreacted 3 and 4 under the same conditions. Compounds Z1-Z7 can be formed with similar yields and enantiomeric efficiency. The removal of the methylketal in 2 was achieved by exposure of 2 to pyridinium p-toluene sulfonate (PPTS) in wet THF at 0° C., which provided FR901464 (1) as a white powder in good yield. The $^1$H and $^{13}$C NMR of our synthetic FR901464[[α]$_D$-13.0 (c 0.45, CH$_2$Cl$_2$)] is identical to the reported spectra of natural [[α]$_D$-12.0 (c 0.5, CH$_2$Cl$_2$)] and synthetic FR901464.

SCHEME 3

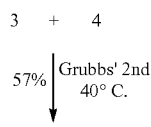

Thus, embodiments of the present invention provide a concise and enantioselective strategy for the syntheses of FR901464, Spliceostatin A, or compounds Z1-Z7 in about 20 total steps with the longest linear sequence of about 10 steps. The syntheses includes the use of readily available chiral pool (R)-isopropylidene glyceraldyhyde 5 to form an A-ring fragment, a CBS reduction, an Achmatowicz rearrangement, and a stereoselective Michael addition for the construction of a B-ring fragment, and a cross-metathesis reaction for coupling the two fragments. The synthesis is short, convergent and amenable to the synthesis of structural variants not disclosed, which are intended to be encompassed in the synthetic methods.

Example 3

The compound of the formula:

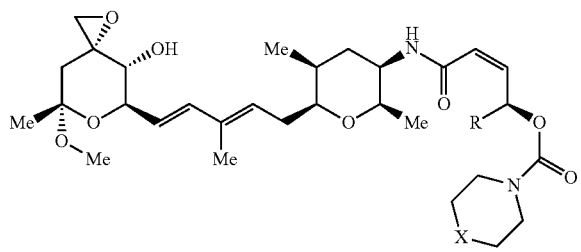

X = O, NH, NMe, CO$_2$Et
R = Me, Et, i-Pr, Ph, Bn was synthesized according to the synthetic scheme shown below in Scheme 4:

Scheme 4
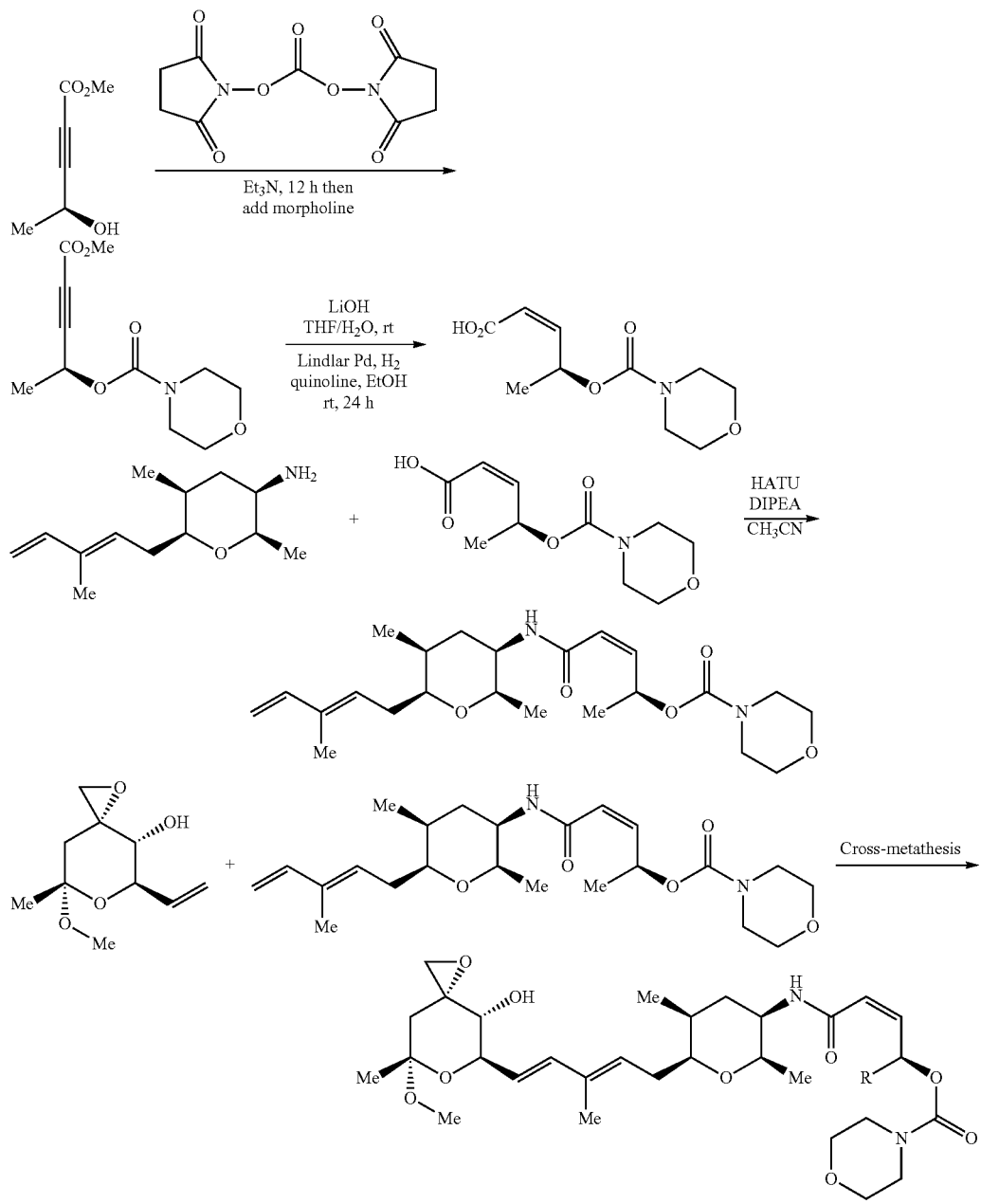
Example 4
The compound of the formulae:
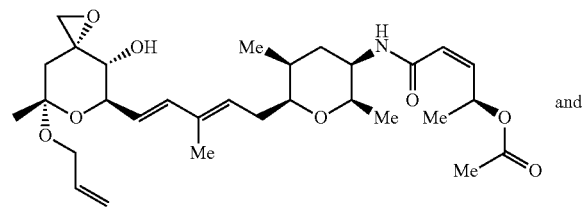 and 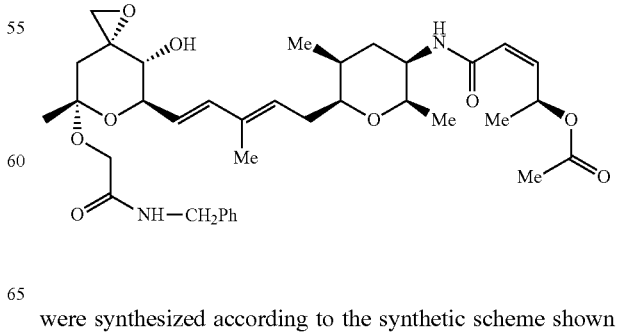
were synthesized according to the synthetic scheme shown below in Scheme 5:

Scheme 5
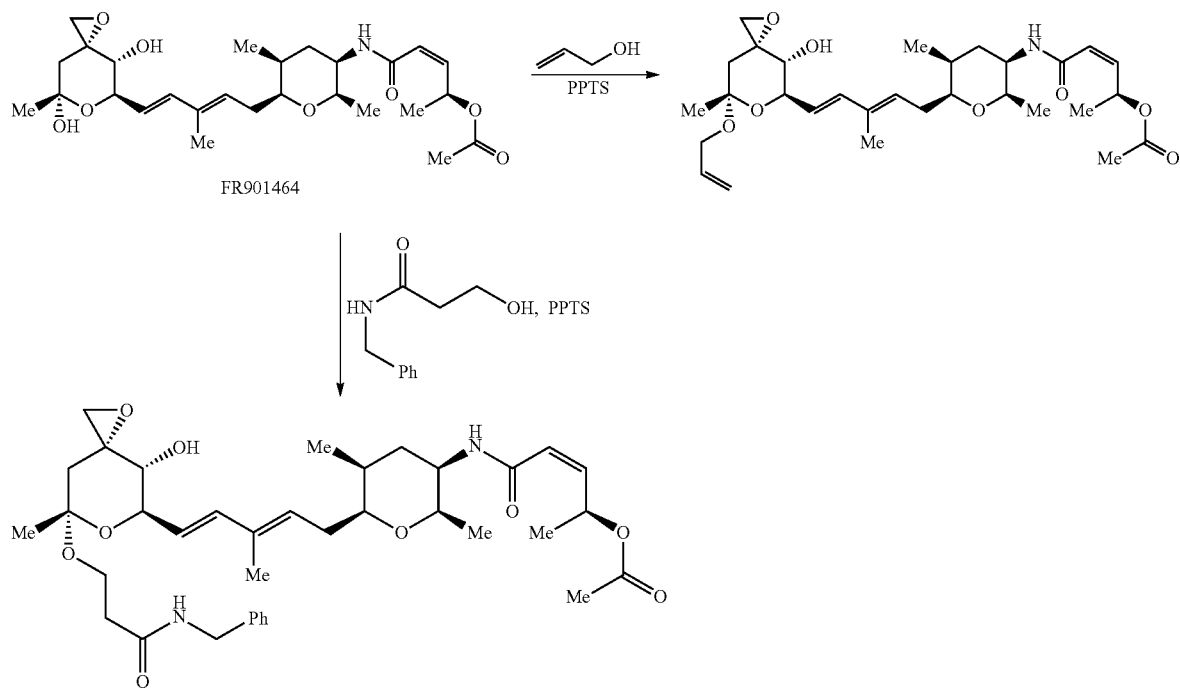
Example 4
The compound of the formula:
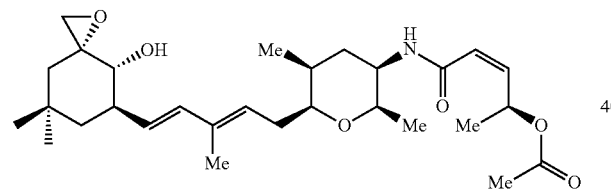
was synthesized according to the synthetic scheme shown below in Scheme 6:
Scheme 6
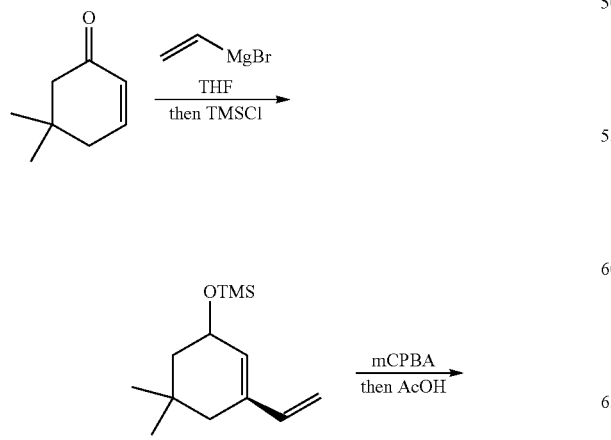
-continued
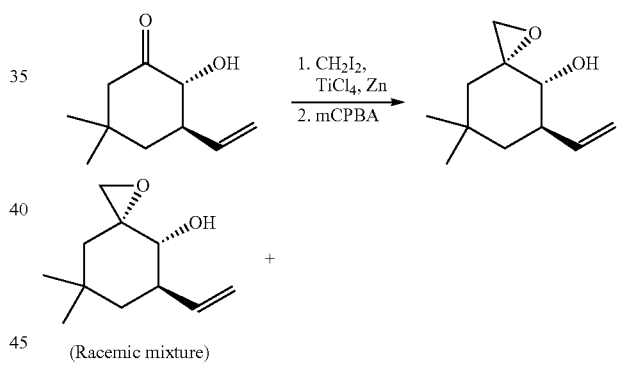
(Racemic mixture)
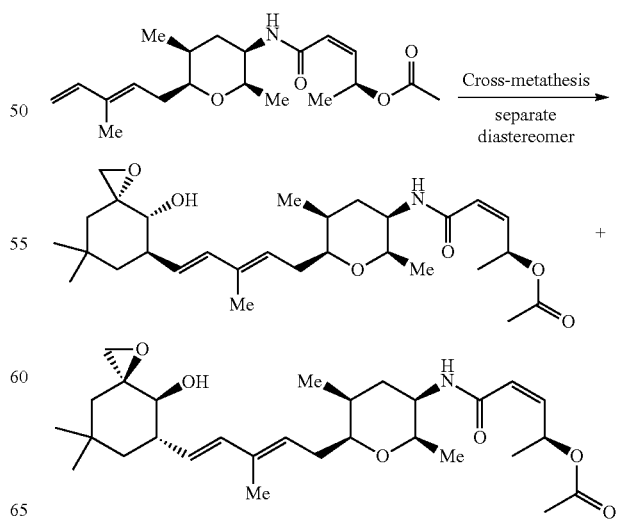

The following embodiments are provided, the numbering of which is not to be construed as designating levels of importance:

Embodiment 1 relates to a process for preparing a compound having Formula I, or a stereoisomer, pharmaceutically acceptable salt, prodrug (e.g., ester) or antibody conjugate thereof:

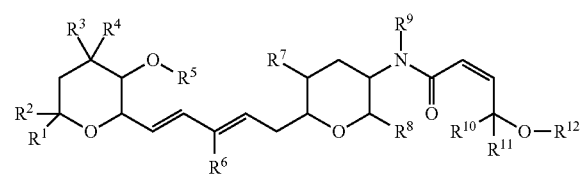
I wherein
$R^1$ and $R^2$ are independently selected from the group consisting of H, OH, $C_{1-6}$-alkyl, $C_{1-6}$-alkoxy, $C_{2-6}$-alkenyloxy, —$(CH_2)_nC(O)NR^{16}R^{17}$ (wherein $R^{16}$ and $R^{17}$ are selected independently from the group consisting of H, $C_{1-6}$-alkyl, and $C_{1-6}$-alkyl substituted with one to three groups independently selected from halo, hydroxy, $C_{1-6}$-alkoxy, and aryl; or $R^{16}$ and $R^{17}$, together with the nitrogen atom to which they are bound, form a 5- to 6-membered heterocyclic or heteroaromatic ring), and $C_{1-6}$-alkyl substituted with one to three groups independently selected from halo, hydroxy, $C_{1-6}$-alkoxy, and O-hydroxy protecting group;

$R^3$ and $R^4$ are selected independently from the group consisting of OH, $C_{1-6}$-alkyl (optionally substituted with Cl, F, $NO_2$, OH, or LG, wherein LG is a leaving group), $C(O)R^{13}$, F, Cl, $NO_2$, wherein each $R^{13}$ is independently H or $C_{1-6}$-alkyl; or $R^3$ and $R^4$, together with the carbon atom to which they are bound, form an epoxide ring;

$R^5$ and $R^{12}$ are independently selected from the group consisting of H, a hydroxyl protecting group, $C_{1-6}$-alkyl, $C(O)R^{13}$, $C(O)OR^{13}$, and $C(O)NR^{14}R^{15}$, wherein each $R^{13}$ is independently H or $C_{1-6}$-alkyl, and wherein $R^{14}$ and $R^{15}$ are selected independently from the group consisting of H and $C_{1-6}$-alkyl; or $R^{14}$ and $R^{15}$, together with the nitrogen atom to which they are bound, form a 5- to 6-membered heterocyclic or hetero aromatic ring;

$R^6$ is selected from the group consisting of H and $C_{1-6}$-alkyl; and $R^7$ is $C_{1-6}$-alkyl;

$R^8$, $R^9$, le, and $R^{11}$ are independently selected from the group consisting of H and $C_{1-6}$-alkyl;

the method comprising converting a compound of the Formula II:

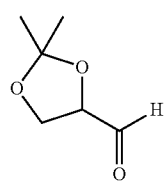
II to a compound of the Formula III:

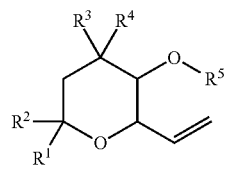
III wherein $R^1$, $R^2$, $R^3$, $R^4$, and $R^5$ are defined herein; and contacting a compound of Formula III with a compound of the Formula IV:

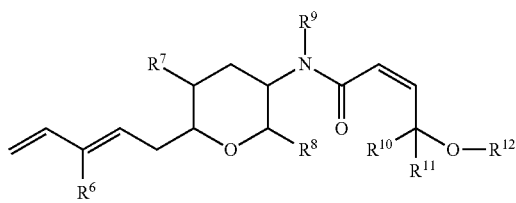
IV wherein $R^6$, $R^7$, $R^8$, $R^9$, $R^{10}$, $R^{11}$, and $R^{12}$ are defined herein; in the presence of an olefin metathesis catalyst to form a compound of Formula I.

Embodiment 2 relates to the process of Embodiment 1, wherein the compound of the Formula III is a compound of the formula:

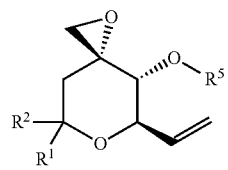
III $R^1$ and $R^2$ are independently selected from the group consisting of H, OH, $C_{1-6}$-alkyl, and $C_{1-6}$-alkyl substituted with one to three groups independently selected from halo, hydroxy, $C_{1-6}$-alkoxy, and O-hydroxy protecting group;

$R^5$ is selected from the group consisting of H, a hydroxyl protecting group, $C_{1-6}$-alkyl, $C(O)R^{13}$, $C(O)OR^{13}$, and $C(O)NR^{14}R^{15}$, wherein each $R^{13}$ is independently H or $C_{1-6}$-alkyl, and wherein $R^{14}$ and $R^{15}$ are selected independently from the group consisting of H and $C_{1-6}$-alkyl; or $R^{14}$ and $R^{15}$, together with the nitrogen atom to which they are bound, form a 5- to 6-membered heterocyclic or heteroaromatic ring.

Embodiment 3 relates to the process of Embodiments 1-2, wherein $R^1$ is H; $R^2$ is $C_{1-6}$-alkyl and $R^5$ is H.

Embodiment 4 relates to the process of Embodiments 1-3, wherein $R^2$ is —$CH_3$.

Embodiment 5 relates to the process of Embodiments 1-4, wherein the compound of the Formula IV is a compound of the formula:

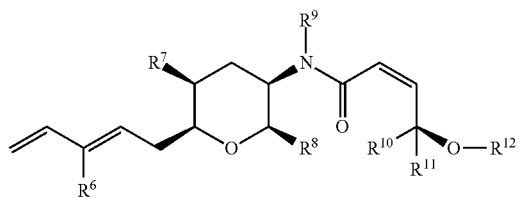

IV $R^6$ is selected from the group consisting of H and $C_{1-6}$-alkyl; and $R^7$ is $C_{1-6}$-alkyl;

$R^8$, $R^9$, $R^{10}$, and $R^{11}$ are independently selected from the group consisting of H and $C_{1-6}$-alkyl; and $R^{12}$ is selected from the group consisting of H, a hydroxyl protecting group, $C_{1-6}$-alkyl, $C(O)R^{13}$, $C(O)OR^{13}$, and $C(O)NR^{14}R^{15}$, wherein each $R^{13}$ is independently H or $C_{1-6}$-alkyl, and wherein $R^{14}$ and $R^{15}$ are selected independently from the group consisting of H and $C_{1-6}$-alkyl; or $R^{14}$ and $R^{15}$, together with the nitrogen atom to which they are bound, form a 5- to 6-membered heterocyclic or heteroaromatic ring.

Embodiment 6 relates to the process of Embodiments 1-5, wherein $R^6$, $R^7$, $R^8$, and $R^{11}$ are independently $C_{1-6}$-alkyl; $R^9$ and $R^{10}$ are H; and $R^{12}$ is $C(O)R^{13}$, wherein $R^{13}$ is $C_{1-6}$-alkyl.

Embodiment 7 relates to the process of Embodiments 1-6, wherein $R^6$, $R^7$, $R^8$, and $R^{11}$ are —$CH_3$; $R^9$ and $R^{10}$ are H; and $R^{12}$ is $C(O)R^{13}$, wherein $R^{13}$ is —$CH_3$.

Embodiment 8 relates to the process of Embodiments 1-7, wherein the compound of the Formula I is a compound selected from the group consisting of:

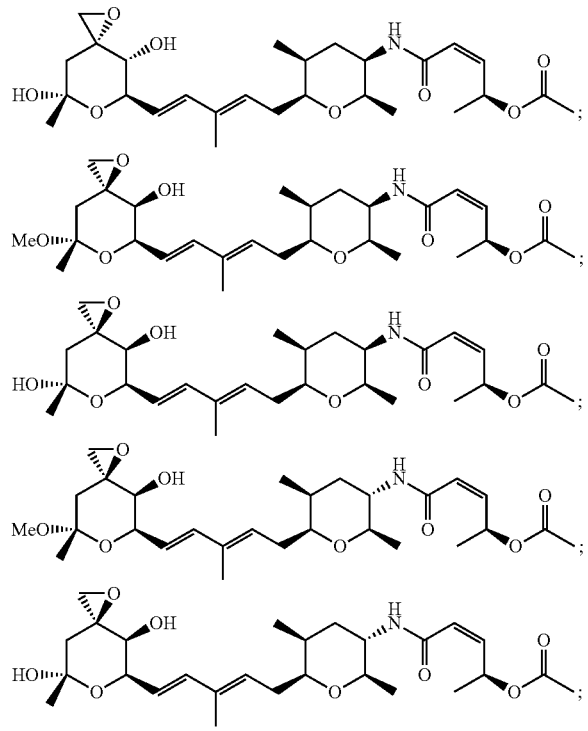

and pharmaceutically acceptable salts, prodrugs or antibody conjugate thereof.

Embodiment 9 relates to a process for preparing a compound having Formula IV, or a stereoisomer, pharmaceutically acceptable salt, prodrug or antibody conjugate thereof:

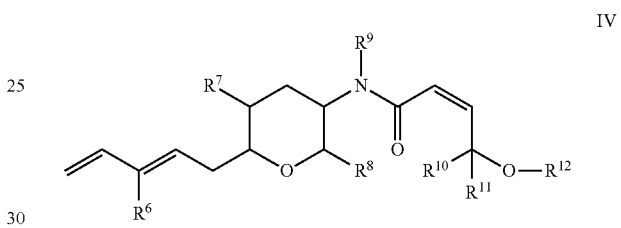

IV wherein $R^6$ is selected from the group consisting of H and $C_{1-6}$-alkyl;

$R^7$ is $C_{1-6}$-alkyl;

$R^8$, $R^9$, $R^{10}$, and $R^{11}$ are independently selected from the group consisting of H and $C_{1-6}$-alkyl; and $R^{12}$ is selected from the group consisting of H, a hydroxyl protecting group, $C_{1-6}$-alkyl, $C(O)R^{13}$, $C(O)OR^{13}$, and $C(O)NR^{14}R^{15}$, wherein each $R^{13}$ is independently H or $C_{1-6}$-alkyl, and wherein $R^{14}$ and $R^{15}$ are selected independently from the group consisting of H and $C_{1-6}$-alkyl; or $R^{14}$ and $R^{15}$, together with the nitrogen atom to which they are bound, form a 5- to 6-membered heterocyclic or hetero aromatic ring;

the process comprising:

contacting a compound of the Formula V:

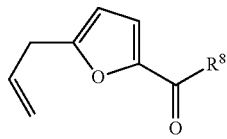

V wherein $R^8$ is defined herein, with a reducing agent to obtain a compound of the Formula VI:

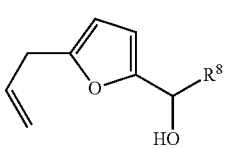

VI wherein R⁸ is defined herein;
contacting the compound of the Formula VI with a metal catalyst to obtain a compound of the Formula VII:

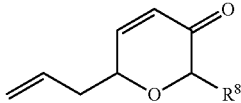

VII wherein R⁸ is defined herein;
contacting the compound of the Formula VII with a compound of the R⁷Li, wherein R⁷ is defined herein, with a metal salt to obtain a compound of the Formula VIII:

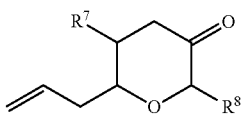

VIII contacting the compound of the Formula VIII with an olefin metathesis catalyst, wherein R⁷ and R⁸ are defined herein, to obtain a compound of the Formula IX:

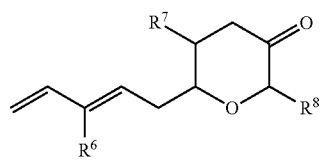

IX wherein R⁷, R⁸, R⁹, R¹⁰, and R¹¹ are defined herein;
converting the compound of the Formula IX to a compound of the Formula X:

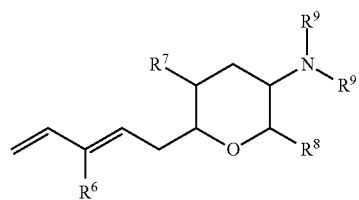

X wherein R⁶, R⁷, R⁸, and R⁹ are defined herein, under reductive amination conditions; and
contacting the compound of the Formula X with a compound of the Formula XI:

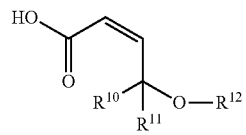

XI wherein R¹⁰, R¹¹, and R¹² are defined herein;
to obtain a compound of the Formula IV.

Embodiment 10 relates to the process of Embodiment 9, wherein the reducing agent is a chiral reducing agent.

Embodiment 11 relates to the process of Embodiment 10, wherein the chiral reducing agent comprises a chiral oxazoborolidine.

Embodiment 12 relates to the process of Embodiment 9, wherein the metal catalyst effects an Achmatowicz rearrangement.

Embodiment 13 relates to the process of Embodiment 9, wherein the metal catalyst is VO(acac)₂.

Embodiment 14 relates to the process of Embodiment 9, wherein the metal salt comprises CuBr.

Embodiment 15 relates to the process of Embodiments 9-14, wherein the compound of the Formula VI is a compound of the formula:

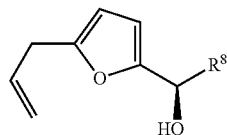

wherein R⁸ is selected from the group consisting of H and C₁₋₆-alkyl.

Embodiment 16 relates to the process of Embodiments 9-15, wherein R⁸ is —CH₃.

Embodiment 17 relates to the process of Embodiments 9-16, wherein the compound of the Formula VII is a compound of the formula:

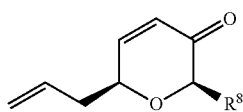

wherein R⁸ is selected from the group consisting of H and C₁₋₆-alkyl.

Embodiment 18 relates to the process of Embodiments 9-17, wherein R⁸ is —CH₃.

Embodiment 19 relates to the process of Embodiments 9-18, wherein, the compound of the Formula VIII is a compound of the formula:

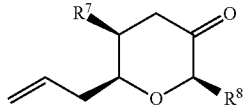

wherein R⁷ and R⁸ are independently C₁₋₆-alkyl.

Embodiment 20 relates to the process of Embodiments 9-19, wherein the compound of the Formula IX is a compound of the formula:

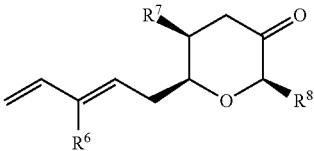

wherein $R^6$ is selected from the group consisting of H and $C_{1-6}$-alkyl;
$R^7$ is $C_{1-6}$-alkyl; and
$R^8$ is selected from the group consisting of H and $C_{1-6}$-alkyl.

Embodiment 21 relates to the process of Embodiments 9-20, wherein the compound of the Formula X is a compound of the formula:

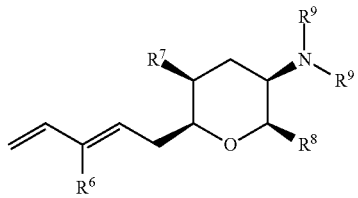

wherein $R^6$ is selected from the group consisting of H and $C_{1-6}$-alkyl;
$R^7$ is $C_{1-6}$-alkyl; and
$R^8$ and $R^9$ are independently selected from the group consisting of H and $C_{1-6}$-alkyl.

Embodiment 22 relates to the process of Embodiments 9-21, wherein the compound of the Formula XI is a compound of the formula:

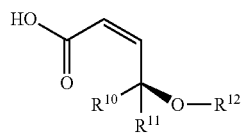

$R^{10}$ and $R^{11}$ are independently selected from the group consisting of H and $C_{1-6}$-alkyl; and
$R^{12}$ is selected from the group consisting of H, a hydroxyl protecting group, $C_{1-6}$-alkyl, $C(O)R^{13}$, $C(O)OR^{13}$, and $C(O)NR^{14}R^{15}$, wherein each $R^{13}$ is independently H or $C_{1-6}$-alkyl, and wherein $R^{14}$ and $R^{15}$ are selected independently from the group consisting of H and $C_{1-6}$-alkyl; or $R^{14}$ and $R^{15}$, together with the nitrogen atom to which they are bound, form a 5- to 6-membered heterocyclic or heteroaromatic ring.

Embodiment 23 relates to the process of Embodiments 9-22, wherein $R^{11}$ is $C_{1-6}$-alkyl; $R^{10}$ is H; and $R^{12}$ is $C(O)R^{13}$, wherein $R^{13}$ is $C_{1-6}$-alkyl.

Embodiment 24 relates to the process of Embodiments 9-23, wherein $R^{11}$ is —$CH_3$.

Embodiment 25 relates to a compound selected from the group consisting of:

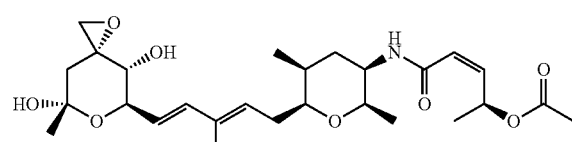

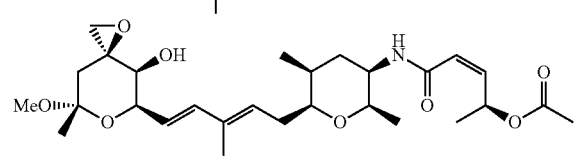

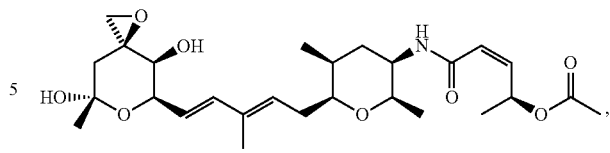

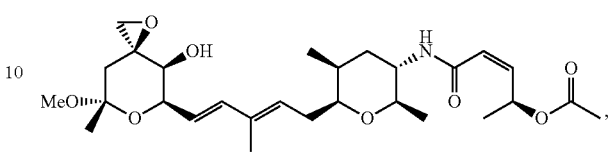

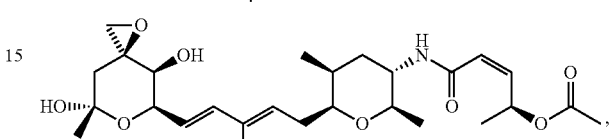

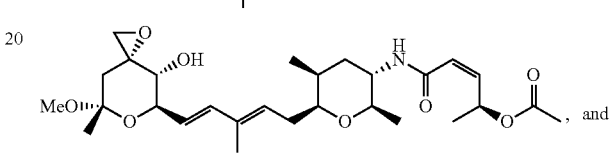, and

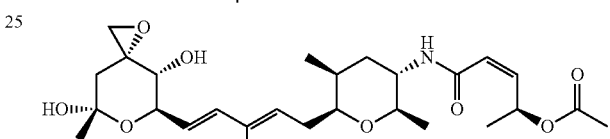

or a salt, prodrug or antibody conjugate thereof.

Embodiment 26 relates to a pharmaceutical composition comprising one or more of the compounds of Embodiment 25, or salts, prodrugs or antibody conjugates thereof, and a pharmaceutically acceptable carrier or excipient.

Embodiment 27 relates to a prodrug that is converted in vivo into a compound selected from the group consisting of:

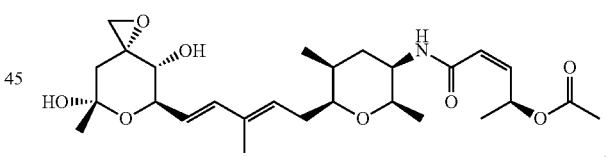

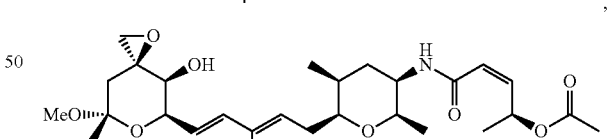

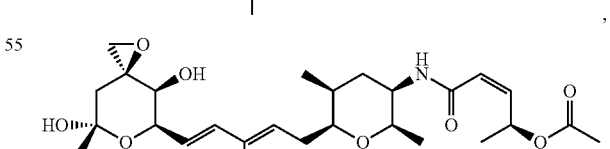

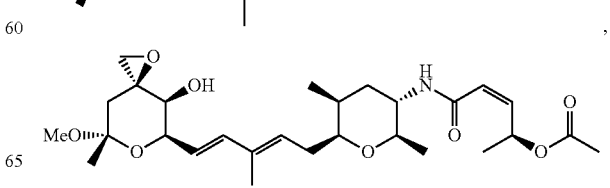

-continued

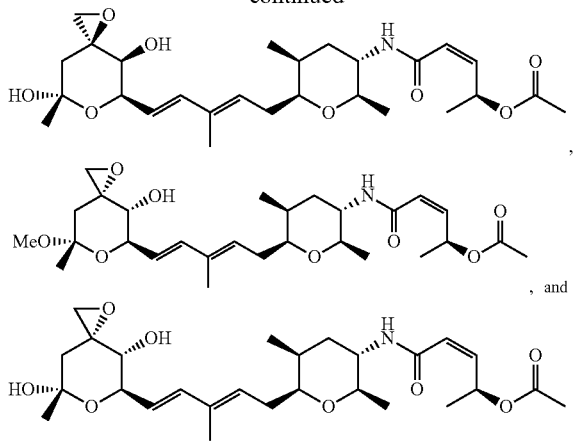
,

Embodiment 28 relates to a method of treating cancer in a subject in need of such treatment, comprising administering a therapeutically-effective amount of one or more compounds of Embodiment 25 or a salt, prodrug or antibody conjugate thereof.

Embodiment 29 relates to the method of Embodiment 28, wherein the cancer is a solid-tumor cancer.

Embodiment 30 relates to the method of Embodiment 28, wherein the cancer is selected from cervical, prostate, lung, ovarian, breast, renal cell, and pancreatic cancers.

Embodiment 31 relates to the method of Embodiments 28-30, wherein a therapeutically-effective amount of the one or more compounds is administered at least twice within a 60 day period.

Embodiment 32 relates to the method of Embodiments 28-31, further comprising administering one or more of the compounds of Embodiment 25 in combination with at least one other anticancer agent.

The invention claimed is:

1. A compound according to Formula I or a pharmaceutically acceptable salt thereof:

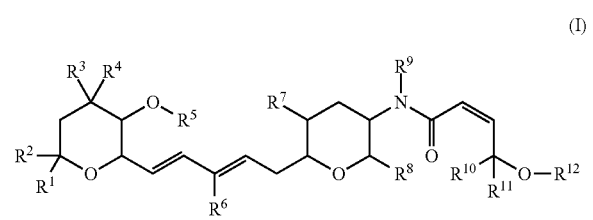

(I)

wherein
R$^1$ and R$^2$ are each independently OH or C$_{1-6}$-alkoxy
R$^3$ and R$^4$, together with the carbon atom to which they are bound, form an epoxide ring;
R$^5$ is selected from the group consisting of H, a hydroxyl protecting group, C$_{1-6}$-alkyl, C(O)R$^{13}$, C(O)OR$^{13}$, and C(O)NR$^{14}$R$^{15}$, wherein each R$^{13}$ is independently H or C$_{1-6}$-alkyl;
R$^6$ is selected from the group consisting of H and C$_{1-6}$-alkyl; and R$^7$ is C$_{1-6}$-alkyl; and
R$^8$, R$^9$, R$^{10}$, and R$^{11}$ are independently selected from the group consisting of H and C$_{1-6}$-alkyl
R$^{12}$ is C(O)NR$^{14}$R$^{15}$ wherein
R$^{14}$ and R$^{15}$ together with the nitrogen atom to which they are bound, form a 5- or 6-membered heterocyclic ring.

2. The compound according to claim 1 or a pharmaceutically acceptable salt thereof, wherein
R$^5$ is selected from the group consisting of H, a hydroxyl protecting group, and C$_{1-6}$-alkyl.

3. The compound according to claim 2 or a pharmaceutically acceptable salt thereof, wherein
R$^5$ is H; and
R$^8$ is C$_{1-6}$-alkyl.

4. The compound according to claim 3 or a pharmaceutically acceptable salt thereof, wherein the compound conforms to the formula:

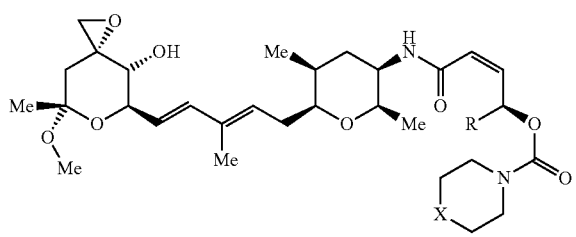

wherein
X is selected from the group consisting of O, NH, and NMe; and
R is selected from the group consisting of Me, Et, i-Pr, phenyl, and benzyl.

5. The compound according to claim 4 or a pharmaceutically acceptable salt thereof, wherein X is NH.

6. The compound according to claim 3 or a pharmaceutically acceptable salt thereof, wherein the compound is:

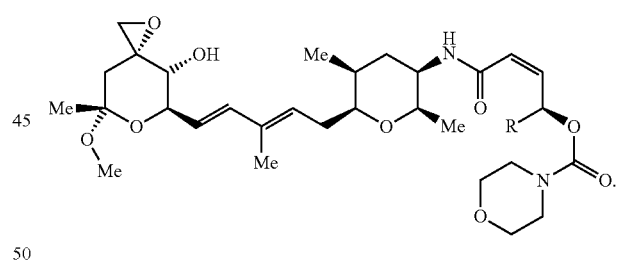

7. An antibody conjugate, comprising at least one compound according to claim 1 conjugated to an antibody.

8. A pharmaceutical composition comprising a therapeutically effective amount of a compound according to claim 1 or a pharmaceutically acceptable salt thereof and one or more pharmaceutically acceptable carriers, diluents, excipients or combinations thereof.

9. A compound according to claim 1 or a pharmaceutically acceptable salt thereof for treating a patient in need of relief from cancer.

* * * * *